United States Patent
Loeb et al.

(10) Patent No.: US 6,181,965 B1
(45) Date of Patent: Jan. 30, 2001

(54) IMPLANTABLE MICROSTIMULATOR SYSTEM FOR PREVENTION OF DISORDERS

(75) Inventors: Gerald E. Loeb; Frances J. R. Richmond, both of Kingston (CA)

(73) Assignee: Advanced Bionics Corporation, Sylmar, CA (US)

(*) Notice: Under 35 U.S.C. 154(b), the term of this patent shall be extended for 0 days.

(21) Appl. No.: 09/490,920

(22) Filed: Jan. 25, 2000

Related U.S. Application Data

(62) Division of application No. 09/077,662, filed on May 29, 1998, now Pat. No. 6,051,017.

(51) Int. Cl.[7] ............................................. A61N 1/00
(52) U.S. Cl. ................................................. 607/3; 607/59
(58) Field of Search ...................... 607/1–3, 46, 48–52, 607/59–61; 128/899; 600/554, 302, 377

(56) References Cited

U.S. PATENT DOCUMENTS

| | | |
|---|---|---|
| 3,971,388 | 7/1976 | Cowdery . |
| 4,026,304 | 5/1977 | Levy . |
| 4,041,955 | 8/1977 | Kelly et al. . |
| 4,524,774 | 6/1985 | Hildebrandt . |
| 4,991,582 | 2/1991 | Byers et al. . |
| 5,094,242 | 3/1992 | Gleason et al. . |
| 5,167,229 * | 12/1992 | Peckham et al. ............... 607/48 |
| 5,193,539 * | 3/1993 | Schulman et al. ............... 607/61 |
| 5,193,540 * | 3/1993 | Schulman et al. ............... 607/61 |
| 5,312,439 | 5/1994 | Loeb . |
| 5,324,316 | 6/1994 | Schulman et al. . |
| 5,405,367 | 4/1995 | Schulman et al. . |
| 5,482,008 | 1/1996 | Stafford et al. . |
| 5,814,089 | 9/1998 | Stokes et al. . |

FOREIGN PATENT DOCUMENTS

| | | |
|---|---|---|
| 0047013 | 10/1982 | (EP) . |
| 2107826 | 9/1971 | (FR) . |
| 9200747 | 1/1992 | (WO) . |
| 9405361 | 3/1994 | (WO) . |
| 9729802 | 8/1997 | (WO) . |

* cited by examiner

*Primary Examiner*—George R. Evanisko
(74) *Attorney, Agent, or Firm*—Bryan R. Gold; Kenneth L. Green

(57) ABSTRACT

Improved implantable microstimulators are covered with a biocompatible polymeric coating in order to provide increased strength to the capsule and to capture fragments of the microstimulator should it become mechanically disrupted. Such coating also makes the microstimulator safer and easier to handle. The coating may include one or more diffusible chemical agents that are released in a controlled manner into the surrounding tissue. The chemical agents, such as trophic factors, antibiotics, hormones, neurotransmitters and other pharmaceutical substances, are selected to produce desired physiological effects, to aid, support or to supplement the effects of the electrical stimulation. Further, microstimulators in accordance with the invention provide systems that prevent and/or treat various disorders associated with prolonged inactivity, confinement or immobilization of one or more muscles. Such disorders include pressure ulcers, venous emboli, autonomic dysreflexia, sensorimotor spasticity and muscle atrophy. The microstimulator systems include external control for controlling the operation of the microstimulators. The control includes memory for programming preferred stimulation patterns for later activation by the patient or caregiver.

2 Claims, 5 Drawing Sheets

IMPLANTABLE MICROSTIMULATOR SYSTEM FOR PREVENTION OF DISORDERS

This application is a Divisional Application of U.S. application Ser. No. 09/077,662, filed May 29, 1998, now U.S. Pat. No. 6,051,017 which application is incorporated herein by reference, and which application was filed in the U.S. under 35 U.S.C. §371 based on international application number PCT/US97/02576, filed Feb. 19, 1997; which international PCT application claimed priority to U.S. Provisional Applications Ser. Nos. 60/011,870; 60/012,019; 60/011,868; and 60/011,869; all filed Feb. 20, 1996.

BACKGROUND OF THE INVENTION

Muscles serve a number of functions, most of which are dependent upon their regular contraction, which is in turn dependent upon their strength and health. For example, in addition to the well known functions of supporting the skeleton and permitting movement, muscles serve to pad the force of bone protuberances against the skin, and they promote blood flow, particularly through deep blood vessels. In response to repeated contractions against a load, muscle fibers grow in cross-sectional area and develop more force, and in response to repeated contraction over a long period of time, the oxidative capacity and blood supply of the fibers is enhanced.

In normal individuals, muscles are activated to contract by electrical signals that are communicated from the brain and spinal cord by way of muscle nerves. Many medical diseases, physical disabilities and cosmetic disfigurements arise from abnormal or absent electrical signals to the muscles. Such abnormal or absent electrical signals may be pathological or may simply be due to prolonged immobility or confinement that restricts or prevents the voluntary movement of one or more muscles. Without normal, routine electrical stimulation, muscles atrophy, that is lose their normal size and strength. Also contributing to muscle atrophy may be a wide range of other pathophysiological mechanisms, including absence of sustaining hormones and other endogenous trophic substances.

Many situations exist in which voluntary muscle contraction cannot be used effectively to operate, condition or strehgthen muscles. The most extreme loss of voluntary muscle function occurs when the brain or spinal cord is injured by trauma, the growth of tumors or cerebrovascular accidents. In patients suffering from these conditions, muscles become wholly or partially paralyzed because the electrical commands that are normally generated in the nervous system are no longer available to stimulate muscle contractions. Less extreme degrees of muscle weakness and atrophy can come about when some of the nerve fibers supplying a muscle are damaged by disease or injury or when the muscle is immobilized or voluntarily rested, for example by casting or bedrest, in order to recover from an injury or surgical intervention involving a nearby body part, or other prolonged confinement or immobilization.

With respect to prolonged physical confinement or immobilization, the affect of muscle non-use and atrophy frequently leads to two disorders that are particularly difficult to avoid and expensive to treat, pressure ulcers of the skin and subcutaneous tissues and retardation of the normal circulation of blood through deep vessels. Continual, unrelieved pressure on localized regions of skin can result in the development of pressure ulcers of the skin and subcutaneous tissues, also known as bed sores or decubitus ulcers. Pressure ulcers are thought to occur when tissues underlying a site of pressure are deprived of oxygen and nutrients because blood flow is impeded, and when the area is subjected to frictional and shearing forces associated with continuous rubbing and movement. Pressure ulcers vary in size and degree of damage from small regions of redness to deep craters of tissue erosion passing through skin, connective tissues, muscle and even bone that can threaten the life of a patient by providing portals of entry for pathogenic organisms. They are often exacerbated in chronically paralyzed or bedridden patients because of atrophy of the unused muscles that normally provide a degree of padding between the skin and underlying bony protuberances. The treatment of pressure ulcers often requires prolonged, intensive medical care and occasionally extensive surgery, usually entailing further restrictions in the posture of the patient, which may further complicate medical and nursing care and cause other complications.

As mentioned above, prolonged immobilization or physical confinement of a body part often also results in retardation of circulation of blood through deep vessels, particularly the veins in an around muscles. For example, the failure to contract muscles in the limbs at regular intervals, as occurs normally when walking or standing, is known to cause stasis of blood in some veins. Venous stasis is a predisposing factor in the formation of clots in the veins. Such deep venous thrombosis further compromises blood flow to the immobilized body part and can be the source of dangerous emboli to the heart and lungs. Thrombosed veins may also become chronically infected, posing a danger of septicemia. Examples of particular populations of patients that are especially at risk for development of pressure ulcers and venous emboli include comatose and obtunded patients, patients who are confined by paralysis to bed or wheelchairs, bedridden patients who have medical or surgical conditions that limit their activity, and elderly patients with limited mobility. To reduce complications in these patients, it is necessary to reestablish movement of the vulnerable body parts; however, these patients are either incapable of voluntary movement or severely restricted in their ability to voluntarily move. Therefore, therapists often spend considerable time manipulating the passive limbs of these patients, but this is expensive and relatively ineffectual because it is the active contraction of muscle that tends to pump blood through the veins and to maintain the bulk of the muscle.

It has long been known that muscle contractions can be elicited involuntarily by stimulating muscles and their associated motor nerves by means of electrical currents generated from electronic devices called stimulators. This has given rise to various therapies that seek to prevent or reverse muscle atrophy and its associated disorders by the application of electrical stimulation to the muscles and their nerves via these stimulators. For example, the field of research known as functional neuromuscular stimulation (FNS) or functional electrical stimulation (FES) has begun, which seeds to design and implement devices capable of applying electrical currentsin order to restore functional movement to paralyzed limbs. Similarly, therapies employing stimulators to regularly apply specific patterns of electrical stimulation to muscles in order to prevent or reverse atrophy are known.

Many of the earliest stimulators were bulky and relied upon the delivery c)f large current pulses through electrodes affixed to the skin, a procedure that requires careful Positioning and fixation of the electrodes to the skin and frequently produces disagreeable cutaneous sensations and irritation ofthe skin. Additionally, such transcutaneous stimulation produces relatively poor control over specific muscles, particularly those that lie deep in the body. Thus, this procedure can be time-consuming, uncomfortable, and is generally useful only for muscles located immediately beneath the skin.

It is also possible to stimulate muscles more directly by passing electrodes through the skin into the muscles or by surgically implanting self-contained stimulators and their associated leads and electrodes in the body. These devices have many configurations, but most are large and have numerous leads that must be implanted and routed through the body to the desired muscles using complex surgical methods. Further, they are expensive to produce and the invasive procedures required for their implantation are impractical for most patients because they increase rather than decrease the required care and the danger of infection and other sources of morbidity in patients who are already seriously ill. Thus, such devices have been used–primarily in patients with severe paralysis in order to demonstrate the feasibility of producing purposeful movements such as those required for locomotion, hand-grasp or respiration.

More recently a new technology has been described whereby electrical signals can be generated within specific tissues by means of a miniature implanted capsule, referred to as a "microstimulator", that receives power and control signals by inductive coupling of magnetic fields generated by an extracorporeal antenna rather than requiring any electrical leads. See, U.S. Pat. Nos. 5,193,539; 5,193,540; 5,324,316; and 5,405,367, each of which is incorporated in its entirety by reference herein. These microstimulators are particularly advantageous because they can be manufactured inexpensively and can be implanted non-surgically by injection. Additionally, each implanted microstimulator can be commanded, at will, to produce a well-localized electrical current pulse of a prescribed magnitude, duration and/or repetition rate sufficient to cause a smoothly graded contraction of the muscle in which the microstimulator is implanted. Further, operation of more than one microstimulator can be coordinated to provide simultaneous or successive stimulation of large numbers of muscles, even over long periods of time.

While originally designed to reanimate muscles so that they could carry out purposeful movements, such as locomotion, the low cost, simplicity, safety and ease of implantation of these microstimulators suggests that they may additionally be used to conduct a broader range of therapies in which increased muscle strength, increased muscle fatigue resistance and/or increased muscle physical bulk are desirable; such as therapies directed to those muscle disorders described above. For example, electrical stimulation of an immobilized muscle in a casted limb may be used to elicit isometric muscle contractions that would prevent the atrophy of the muscle for the duration of the casting period and facilitate the subsequent rehabilitative process after the cast is removed. Similarly, repeated activation of microstimulators injected into the shoulder muscles of patients suffering from stroke would enable the paretic muscles to retain or develop bulk and tone, thus helping to offset the tendency for such patients to develop subluxation at the shoulder joint. Use of microstimulators to condition perineal muscles as set forth in applicant's copending patent application, Ser. No. 60/007,521, filed Nov. 24, 1995, entitled "Method for Conditioning Pelvic Musculature Using an RF-Controlled Implanted Microstimulator", incorporated herein by reference, increases the bulk and strength of the musculature in order to maximize its ability to prevent urinary or fecal incontinence.

In addition to the therapeutic use of microstimulators to promote contraction of specific, isolated muscles in order to prevent or remedy the disorders caused or contributed to by inactive muscles, the administration of hormones, trophic factors and similar physiologically active compounds may also be useful. It is known that the extent to which a muscle will grow in response to any stimulation regime is affected by the hormonal and chemical environment around the muscle. Muscle fibers have receptors for many physiologically active compounds that circulate normally in the blood stream or are released from nerve endings. These trophic factors have significant effects on the nature, rate, and amount of growth and adaptation that can be expected of the muscle in response to stimulation, whether such is produced voluntarily or by electrical stimulation. Perhaps the best known of these hormones are the androgenic steroids often used by athletes to increase muscle bulk and strength; but other hormones such as estrogens and growth hormones are also known to affect muscle properties. For example, the dramatic reductions in circulating estrogens and androgens that occur in women following menopause appear to account for decreases in the mass of muscles and bones, which can be slowed or even reversed by administering the deficient hormones systemically.

Thus, the beneficial strengthening effects of electrical stimulation can be maximized by providing the affected muscles with a supportive hormonal environment for growth. These compounds can be provided systemically by administering them orally or by injection. However, many such compounds are rapidly metabolized by the liver, so that high doses must be administered to achieve a desirable therapeutic effect. This can expose all tissues of the body, including the liver, to high and perhaps poorly controlled levels of the compound, resulting in undesirable side-effects that may outweigh the desired actions of the agent. In one aspect, the present invention recognizes that this problem could be circumvented by using a more selective method of drug delivery directed specifically to the electrically exercised muscles. Even if the introduced compound were ultimately to be cleared by absorption into the bloodstream, high concentrations would be produced only in the tissue around the target. A steep dilutional gradient would ensure that other regions of the body were exposed to much lower levels of the administered compound. By providing a more conducive chemical environment in the early stages of electrical therapy, it is expected that muscle atrophy could be reversed more rapidly and effectively. After muscle function has been reestablished, longer-term performance of the muscle could be more easily maintained at the desired level by electrical stimulation alone or in combination with low-dose systemic replacement therapy.

The microstimulators described and claimed herein are elongated devices with metallic electrodes at each end that deliver electrical current to the immediately surrounding biological tissues. The microelectronic circuitry and inductive coils that control the electrical current applied to the electrodes are protected from the body fluids by a hermetically sealed capsule. This capsule is typically made of a rigid dielectric material, such as glass or ceramic, that transmits magnetic fields but is impermeable to water vapor.

Encapsulation in glass is an effective and inexpensive way to ensure a hermetic seal between the electronic components and the biological tissues. Methods for forming similar hermetic seals within the confined dimensions of the overall device are well-known in the fabrication of industrial magnetic reed relays and diodes and have been described specifically for implantable microstimulators. See, e.g., U.S. Pat. Nos. 4,991,582; 5,312,439; and 5,405,367, each of which is incorporated in its entirety by reference herein.

Such a hermetic barrier is important both to ensure good biocompatibility with the body and to protect the sensitive electronics from the body fluids that might destroy their function.

Unfortunately, however, glass and similarly brittle materials such as ceramic may crack or shatter as a result of externally applied forces or even residual stress in the crystalline structure of the material itself. If such an event occurs within the body or during a surgical procedure, it is desirable to retain or capture the sharp fragments of the capsule and any internal components so that they do not irritate or migrate into the surrounding tissues. In a testing or surgical environment in which devices are handled repeatedly, the hard, slippery surface of the glass capsule makes the device difficult to handle, and could increase the likelihood that the device will be dropped or pinched with a force sufficient to break the glass. Therefore, in one aspect, the present invention provides a well-chosen biocompatible coating for the glass which would decrease the lubricity of the device and ensure that glass pieces resulting from device fracture would be contained/captured in a protective sleeve.

The reaction of a living body to an intact foreign body such as an implanted microstimulator depends at least in part on the shape and texture of the surface of the foreign body, as described, e.g., by Woodward and Saithouse (1986). The surfaces left by the manufacturing processes used for the implanted microstimulator are constrained by the nature of the materials and processes required to achieve the desired electronic and mechanical characteristics of the device. Therefore, modification of the microstimulators' chemical nature and/or superficial physical contours to avoid, prevent and/or discourage an immunological response by the body, would be advantageous. Additionally, in selecting an appropriate coating material the opportunity arises for the introduction of various chemical compounds, such as trophic factors and/or hormones, as discussed above, into or onto the coating. Such compounds could then diffuse from the surface of the coating into the surrounding tissues for various therapeutic and diagnostic purposes, as previously mentioned.

SUMMARY OF THE INVENTION

The present invention provides for the prevention and treatment of various disorders caused or exacerbated by abnormal or absent electrical signals to the muscles and apparatus useful therefore. In one aspect, the invention provides an improved microstimulator having a biocompatible polymeric coating on portions of its exterior, thereby reinforcing the mechanical strength of the microstimulator such that it may optionally be implanted deeply into the muscle, while also providing a means for capturing the fragments of the microstimulator should mechanical disruption occur. In preferred embodiments, the coatings provided herein are selected to improve the nature of the foreign body reaction to the implanted microstimulator by modifying its chemical surface, texture and/or shape.

The implantable microstimulators disclosed and claimed herein are preferably of a size and shape that allows them to be implanted by expulsion through a hypodermic needle or similar injectable cannula. The microstimulator includes a hermetically-sealed housing, at least two exposed electrodes, and electronic means within the housing for generating an electrical current and applying the electrical current to the exposed electrodes. The coating, as described in detail herein, is formed on at least a portion of the exterior of the microstimulator in contact with the hermetic seal.

In another aspect of the present invention, the improved microstimulator, in addition to providing electrical stimulation to the muscle within which it is implanted, is modified to provide a locally high level of one or more desired chemical agents or drugs. In a preferred embodiment, the polymeric coating covering a portion of the microstimulator's surface contains a chemical agent that is released gradually from the coating. Thus, when the microstimulator is implanted within or adjacent to a muscle it produces an electrical current that activates the motor nerves and/or muscle fibers of the muscle while simultaneously dispensing the chemical agent(s) in the vicinity of the active muscle fibers.

Further, in preferred embodiments, the improved microstimulator is designed to provide electrical stimulation over a period of many years and to provide elution of the chemical agent(s) over a period of many days, weeks or longer without any percutaneous connections to the external world. Release of the chemical agent from the coating of the microstimulator may be by diffusion or, alternatively, may be at a predetermined rate controlled by electrical signals produced by the implantable device.

In yet another aspect of the present invention, systems providing involuntary movement to muscles for the purpose of preventing, treating and/or slowing the progress of various complications associated with muscle inactivity, especially inactivity due to prolonged physical confinement or immobilization, are provided. These systems employ one or more microstimulators non-surgically implanted in or near one or more inactive muscles. Once implanted, the prescribing physician uses an external controller to command each of the implanted microstimulators to produce various output stimulation pulses in order to determine a pattern of stimulation that produces the desired muscle contraction pattern. The external controller retains the programmed stimulation routine and, thereafter, administers the therapy on a regularly scheduled basis and/or whenever commanded to do so by the patient or any caregiver.

The systems provided herein are particularly useful for maintaining or improving the functional capacity of paralyzed, weak, immobilized or under-exercised muscle without requiring voluntary exercise and for preventing various complications of prolonged physical confinement, including but not limited to pressure ulcers, deep venous thrombosis, autonomic dysreflexia and sensorimortor spasticity. For example, the implantable microstimulators are employed to stimulate specific muscles in order to reduce the incidence and accelerate the healing of pressure ulcers on the sacrum heels and other bony protuberances of bedridden or immobilized patients. Alternatively or additionally, the systems are employed to reduce the possibility of venous stasis and embolus formation by eliciting regular muscle contractions in the legs of the bedridden or otherwise immobilized patient. Advantageously, these systems may be employed to produce the desired pattern of regular contractions in one or more muscles for periods of days or weeks without the need for ongoing, continuous patient or caregiver supervision.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
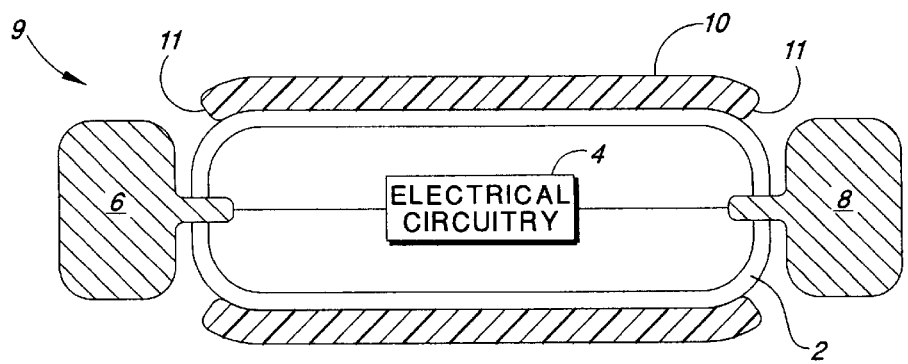
FIG. 1 diagrammatically illustrates one embodiment of a microstimulator coated with a polymeric coating in accordance with the present invention.

An implantable device 9 made in accordance with the present invention is illustrated in FIG. 1. The device 9 includes a narrow, elongated capsule 2 containing electronic circuitry 4 connected to electrodes 6 and 8, which pass through the walls of the capsule at either end1 together forming a microstimulator of the type disclosed and fully described in U.S. Pat. Nos. 5,193,539; 5,193,540; 5,324,316 and 5,405,367, each of which is incorporated herein, in its entirety, by reference. A coating 10 is applied over the longitudinal extent of the surface of the capsule 2. In the particular embodiment of FIG. 1, the ends of the coating 11 do not extend over the surface of electrodes 6, 8, so that the coating does not change the overall profile of the microstimulator. The device 9 is shaped to per—-it its insertion through a tubular insertion cannula, such as a syringe, that can be passed transcutaneously into a target muscle with or without fluoroscopic guidance, as described further below.

The capsule 2 may be made of glass or a similar dielectric material, such as ceramic, that can provide a hermetic barrier to the permeation of body fluids and water vapor into circuitry 4. The basic design of the current-generating circuitry 4 is the same or similar to that described in the above-referenced patents, in which electrodes 6 and 8 may be continuously charged (through inductive coupling) by a programmable magnitude of direct current and may be occasionally discharged so as to produce a large, brief stimulation pulse with a programmable magnitude and duration, which stimulation pulse is used for the activation of nearby motor nerve and/or muscle fibers.

The coating 10 of the improved microstimulator is selected to both be biocompatible and to be elastic enough to provide some reinforcement to the capsule 2. Additionally, it is advantageous and preferred that the material chosen to form the coating 10 serve to reduce the risk of injury from and to provide means for the capture of capsule fragments in the event the capsule is broken. Finally, it is desirable that the coating 10 chosen reduces the lubricity of the device, as glass and ceramic materials, of which the capsule 2 is most often constructed, are slippery. It will be appreciated by those of skill in the art that several different coatings are available having these characteristics. By way of example only and in no way to be limiting, the polymeric coating 10 may be formed of a silicone elastomer or a thermoplastic material, such as polyethylene, polyester, polyurethane or a fluorinated carbon chain from the TEFLON family.

The preferred method of application of coating 10 or depends on its chemical composition and physical properties. For example, in one embodiment, the coating 10 is formed from a thin-walled extrusion of silicone elastomer whose inside diameter is slightly smaller than the outside diameter of capsule 2. The extruded tubing is cut to the desired length and its diameter temporarily expanded by absorption of an appropriate solvent such as heptane, toluene or xylene. The expanded silicone tubing is then slipped over the microstimulator, subsequently shrinking tightly onto the surface of the microstimulator as the solvent is evaporated from the silicone elastomer, thereby forming the desired coating 10.

In another embodiment, the coating 10 is made from a thermoplastic material such as a polyethylene, polyester, polyurethane or a fluorinated carbon chain from the Teflon family. A thin-walled extrusion of such thermoplastic material whose inside diameter is smaller than the outside diameter of capsule 2 is mechanically expanded so as to temporarily increase its inside diameter. The expanded extrusion is then cut to the desired length, slipped over the microstimulator, and caused to shrink onto the surface of the microstimulator by briefly heating it to the temperature at which it contracts toward its unexpanded dimensions, thereby forming the desired coating 10.

In another embodiment1 coating 10 is made from~.B liquid solution containing melted, dissolved or unpolymerized material which is applied to the surf ace of the microstimulator by dip-coating, injection molding, or other suitable methods known to those of skill in the coating art. After covering the desired portions of the microstimulator, the coating 10 is allowed or caused to harden by appropriate means.

Figure 2:
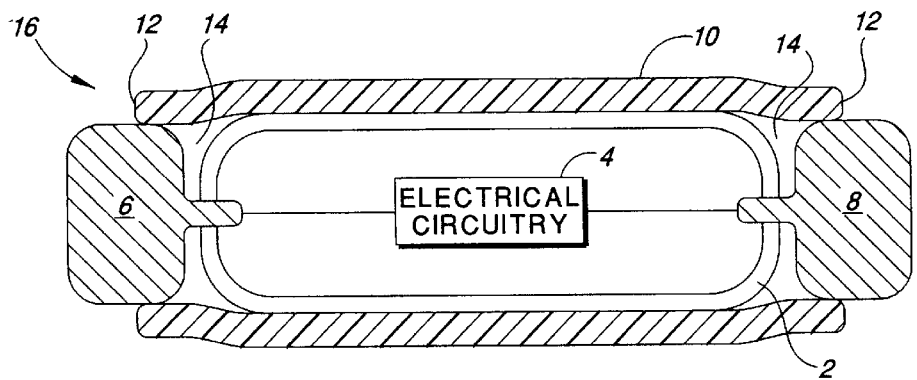
FIG. 2 shows another embodiment of a microstimulator coated with a polymeric coating wherein the coating extends over a portion of the electrodes.

FIG. 2 shows an alternative embodiment of a microstimulator 16 in accordance with the present invention. The microstimulator 16 of FIG. 2 is similar to the microstimulator 9 of FIG. 1 except that in FIG. 2 the ends 12 of coating 10 extend over electrodes 6, 8, thereby preventing concavities 14 from coming into direct contact with tissues surrounding the implanted microstimulator. Advantageously, concavities 14 may be filled with a solid material, such as silicone or other material, to eliminate the presence of pockets of fluid that may act as a nidus of chronic infection.

Figure 3:
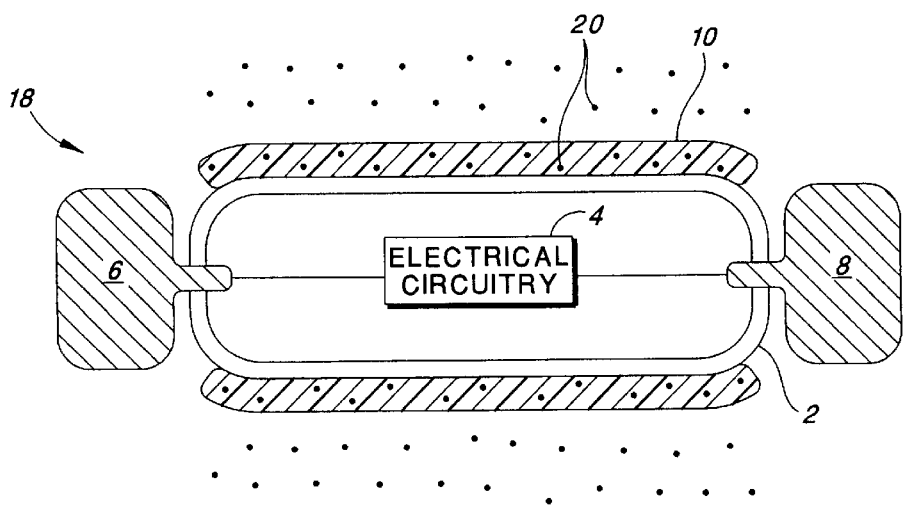
FIG. 3 illustrates another embodiment of the implantable device of the present invention that provides both electrical stimulation and release of a chemical agent.

FIG. 3 shows another embodiment of an improved microstimulator 18 in accordance with the present invention. The microstimulator 18 of FIG. 3 is similar to the microstimulator 9 of FIG. 1 except that the coating 10 in FIG. 3 contains a chemical agent 20 which diffuses from the surface of the coating 10 into the surrounding tissues. The chemical agent 20 may be any of a large number of pharmacologic and diagnostic agents whose presence in the tissue surrounding the implantable microstimulator is desired as part of the treatment received by the patient. Examples of suitable chemical agents 20 include anti-inflammatory or antibiotic compounds intended to reduce the foreign body reaction, hormones, neuromodulators and neurotransmitters intended to potentiate the effects of the electrical currents, or dyes intended to mark the original location of the implanted microstimulator. This list of agents provides only examples and is not intended to limit the scope of the invention set forth in the claims.

The method of introduction of the chemical agent 20 into or onto the coating 10 depends upon the chemical nature of the agent and the selection of an appropriate coating material. In general, the types of agents and compatible coatings that may be used therewith are known to those of skill in the arts of chemical binding and diffusion and the design of sustained release pharmaceuticals.

In a preferred embodiment, the chemical agent 20 comprises a long-acting compound of testosterone, such as testosterone propionate, cypionate or enanthate. This agent 20 is mixed with or adsorbed onto a silicone elastomer that is injection-molded or dip-coated and subsequently polymerized to provide a thin coating 10, which coating 10 is spread over a substantial portion of the surface area of the capsule 2. It should be appreciated that silicone is a highly biocompatible compound that has been used previously to administer steroids to experimental animals without exposing the animals to the trauma of repeated injections. However, it should also be appreciated that coating 10 could be formed from a variety of other materials, or by using a variety of other processes, as described above.

It is thus seen that in this preferred embodiment, agent 20 comprises a trophic compound used to enhance muscle development, specifically a testosterone derivative. It should be appreciated that such compounds have been used for many years in humans to treat endocrine disorders or to retard the development of estrogen-sensitive mammary tumors, and that a single intramuscular bolus of the compound will exert its actions for 2 to 4 weeks. The chemical agent 20 associated with the external coating 10 of the present invention, however, could be selected from a variety of trophic chemicals with actions on muscle or connective tissues, and could be bound to the coating in any manner that advantageously affects its rate of release. The rate of release may be designed to be anywhere from a few hours to a few days or weeks. Furthermore, agent 20 might actually consist of a multiplicity of active compounds1 various of which affect or influence muscle fibers, nerve fibers, connective tissue, or inflammatory cells so as to modify many aspects of the response of the tissues to the presence and activation of the device.

Certain composite materials, such as the drug-filled polymeric matrix that may be used for coating 10 the device, have the property that electrical voltage influences a change in the rate at which the fillers diffuse form the matrix. Where it is desirable to use such compositions, the microstimulator illustrated in FIG. 2 is particularly useful, as the electrical output signals generated by circuit 4 are applied, at least in part, to the coating 10 by its contact with the electrodes 6, 8 of the device. Such electrical output signals are systematically varied so as to produce the desired rate of elution of the chemical agent 20 into the tissues surrounding the implanted device. Thus, it is seen that the electrical currents produced by electrodes 6 and 8 in the process of stimulating the muscle could also advantageously have the effect of increasing the elution rate of agent 20 simultaneously with the electrically-induced muscle contraction.

Figure 4:
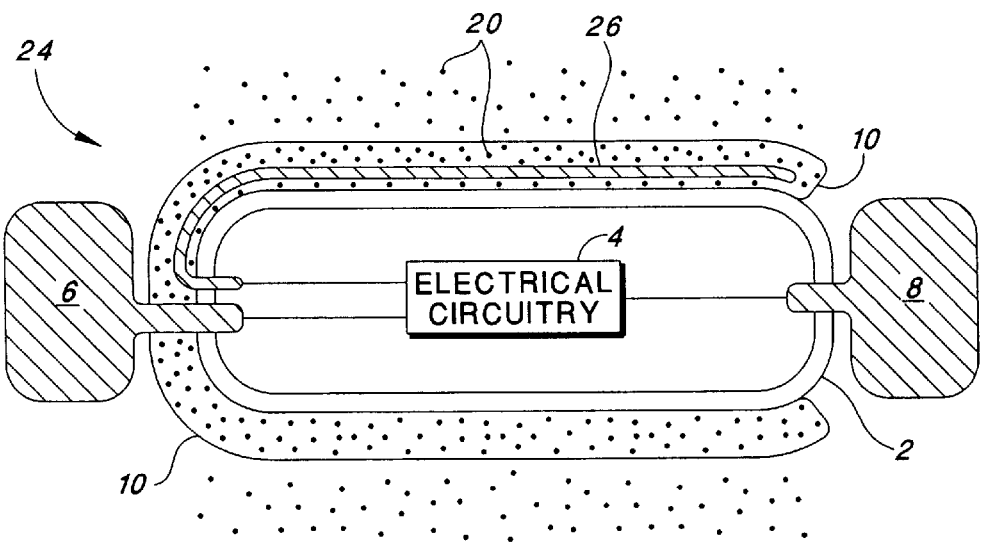
FIG. 4 shows another embodiment of an implantable device in accordance with the present invention.

As illustrated in FIG. 4, rate control of the elution of the chemical agent 20 from the coating 10 may alternatively be managed using additional electrodes 26 which are affixed to the capsule 2 and connected to the circuitry 4 of the device. Such additional electrodes provide for separate control of the electrical currents and voltages applied to stijiulate the muscle electrically and to control the rate of elution of chemical agent 20 from the polymeric coating 10. Advantageously, such multiple electrodes facilitate the use of electrophoretic current through coating 10 to effect the release of agent 20, independent of the currents required to charge and discharge those electrodes associated with muscle or nerve stimulation. As illustrated in FIG. 4, electrode 26 is entirely covered by the polymeric coating 10, whereas electrodes 6 and 8 are exposed to the body fluids. Electrical current applied between electrodes 26 and 8 would pass through coating 10 to effect electrophoretic release of chemical agent 20. Electrical current applied between electrodes 6 and 8, on the other hand, would pass unobstructed through the body fluids and tissues to effect electrical stimulation of nearby nerve or muscle fibers.

Figure 5:
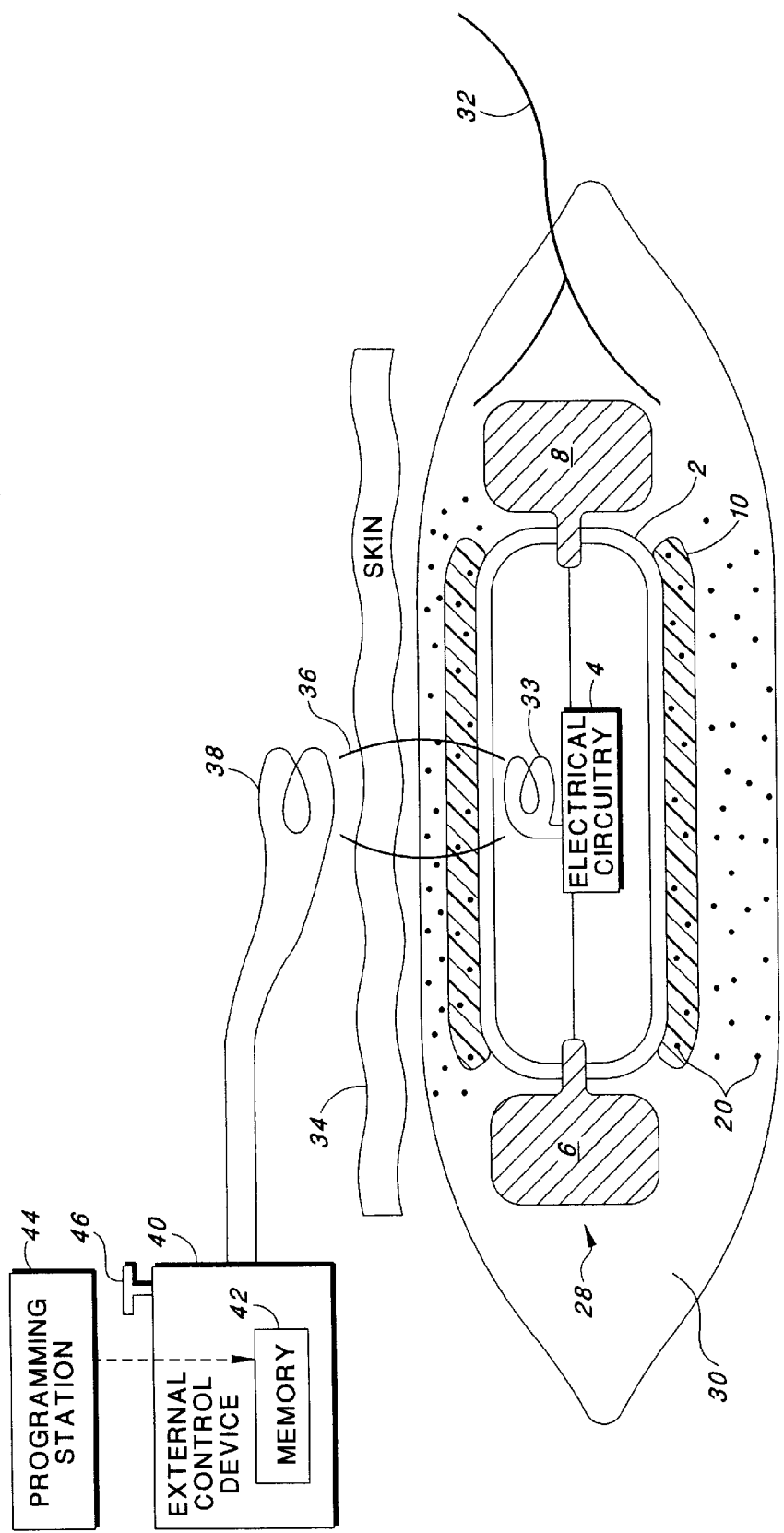
FIG. 5 diagrammatically illustrates an 5 implanted microstimulator in muscle tissue and its control using an external controller.

Referring now to FIG. 5, an improved microstimulator 28 is shown implanted into muscle 30. In this embodiment, as well as in those of FIGS. 1–3, the improved microstimulator receives power form an external control device 40. The external control device 40 generates an alternating magnetic field, illustrated symbolically by the lines 36, through an external coil 38, which coil may advantageously be located underneath the patient in a seat or mattress pad or in a garment or item of bedclothes. The magnetic field 36 is coupled with an implanted coil 33, which forms part of the microstimulator device 28, and induces a voltage and current within the coil 33. The induced voltage/current in the coil 33 is used to power the electronic circuitry 4, and fluctuations (e.g., modulation) of the varying magnetic field 36 are used to control operation of the electronic circuitry 4. That is, the device 28 delivers current to its electrodes 6, 8 according to instructions encoded in fluctuations of the magnetic field 36. In this preferred embodiment, electrical current emitted from electrodes 6 and 8 stimulates motor nerve fibers 32. Muscle fibers themselves are relatively difficult to activate via such electrical currents, but the motor nerve fibers are more readily stimulated, particularly if the microstimulator is located near them in the muscle. Each time a motor nerve fiber is excited, it conveys an electrical impulse through its highly branched structure to synaptic endings on a large number of muscle fibers, which results in the activation of essentially all of those muscle fibers. Electronic circuit 4, then, controls the amplitude and duration of the electrical current pulse emitted by the microstimulator 28, thereby determining the number of such motor nerve fibers that are excited by each pulse.

As an example of a preferred use of the improved microstimulator, the prescribing physician uses a programming station 44 to command external controller 40 to produce various stimulation pulses, during the initial treatment session after implantation of the improved microstimulator 28. This is done in order to determine an exercise program that will provide the desired therapeutic muscle contraction program for the individual patient. The exercise program is down-loaded into a memory element 42 of the external controller 40, where it can be reinitiated at will by, for example, manually activating control 46. This manual control may be performed, e.g., by the patient or an attending caregiver. In the preferred embodiment, programming station 44 is a personal computer, external controller 40 contains a microprocessor, and memory element 42 is a nonvolatile memory bank such as an electrically programmable read-only memory (EEPROM). However, it will be appreciated by those of skill in the art that many different systems, architectures and components can achieve a similar function.

Figure 6:
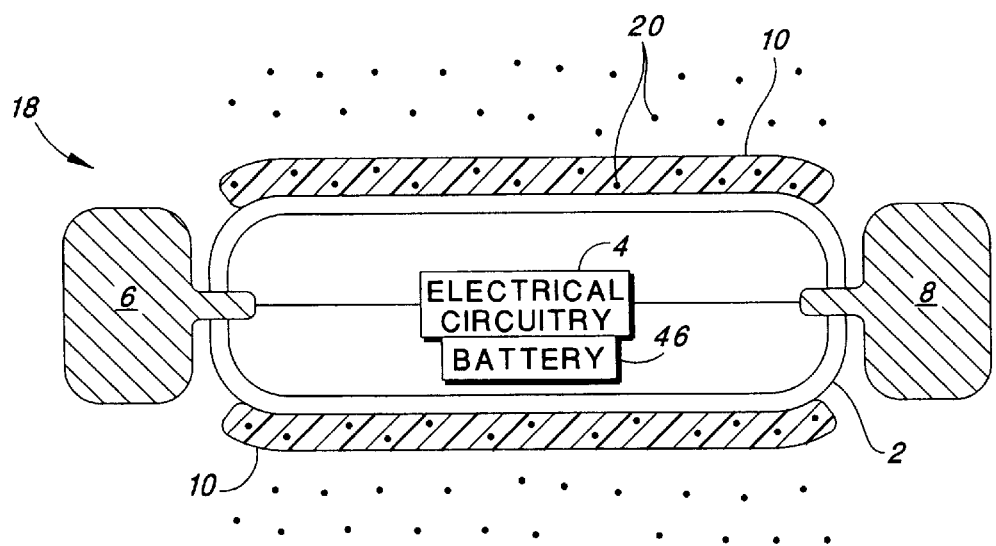
FIG. 6 shows a variation of the invention wherein a battery is included within the implantable device to allow it to operate independently of the external controller.

In accordance with a variation of the invention, shown in FIG. 6, a battery 46 is included within the implanted device (microstimulator), and is employed as a continuous source of power for the electronic circuit 4. Such battery also provides storage and production means for a program of output currents and stimulation pulses that may then be produced autonomously by the implanted device without requiring the continuous presence of extracorporeal electronic components, i.e., without the need for an external control device 40. In such instance, means would be provided for transmitting the desired program to each microstimulator and for commanding each microstimulator to begin or to cease operating autonomously. Advantageously, such an embodiment as shown in FIG. 6 may provide for continuous biasing current or voltage applied to coating 10 (when at least one of the electrodes is positioned to contact the coating 10, as shown in FIG. 2 above, or when a separate electrode is embedded in the coating 10 as illustrated in FIG. 4, above) so that the rate of elution of agent 20 would always be well-controlled.

Figure 7:
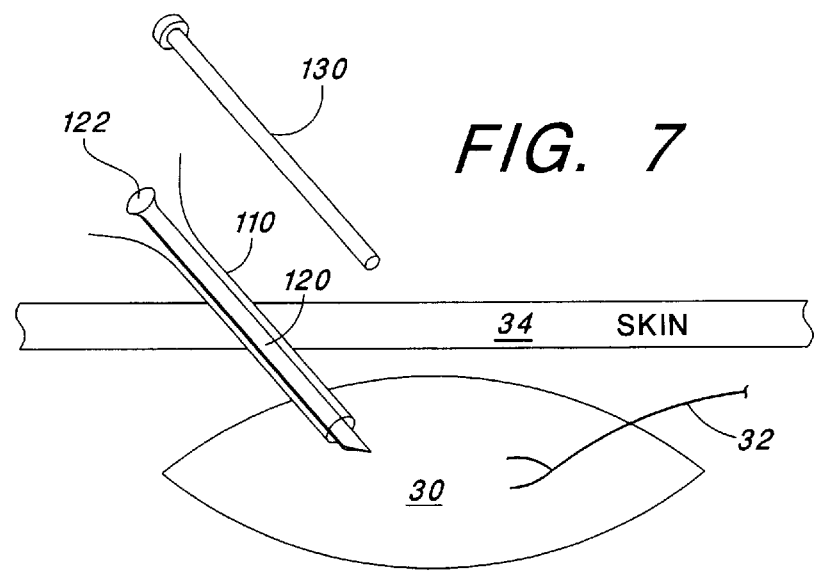
FIG. 7 illustrates a preferred manner used to implant a microstimulator in accordance with the present invention.

In a preferred implantation method, the microstimulator is injected into the muscle of interest through an insertion device whose preferred embodiment is shown in FIG. 7. The external cannula 110 of the insertion tool is comprised of a rigid, dielectric material with sufficient lubricity to permit the easy passage of the microstimulator without scratching its external surface. The central trochar 120 of the insertion tool is an electrically conductive rod whose sharpened point extends beyond the insertion cannula, where it can be used to deliver current pulses to the biological tissue near its point. The initial insertion of the tool is directed either by a knowledge of musculoskeletal landmarks or radiographic imaging methods to approach the region of muscle 30 in which motor nerve fibers 32 enter. Optimally, the insertion device is advanced into the muscle in parallel with the long axis of muscle fiber fascicles. Electrical stimuli may be delivered through the metallic trochar by connecting a conventional electrical stimulator (not shown) to connector 122 on the trochar. By observing the contractions of the muscle 30, these test stimuli can be used to ensure that the tip of the insertion device is situated sufficiently close to motor nerve fibers 32 to permit activation of a substantial portion of the muscle 30 without undesirable activation of other muscles or nerves. Failure to elicit the desired muscle contractions would suggest a poor site of placement for the microstimulator and a need to reposition the insertion tool closer to the site of motor nerve entry.

When the desired position is reached, the trochar 120 is removed from cannula 110, taking care to keep the cannula 110 in position within muscle 30, and a microstimulator is pushed through cannula 110 and into muscle 30 using a blunt-ended push-rod 130.

Figure 8:
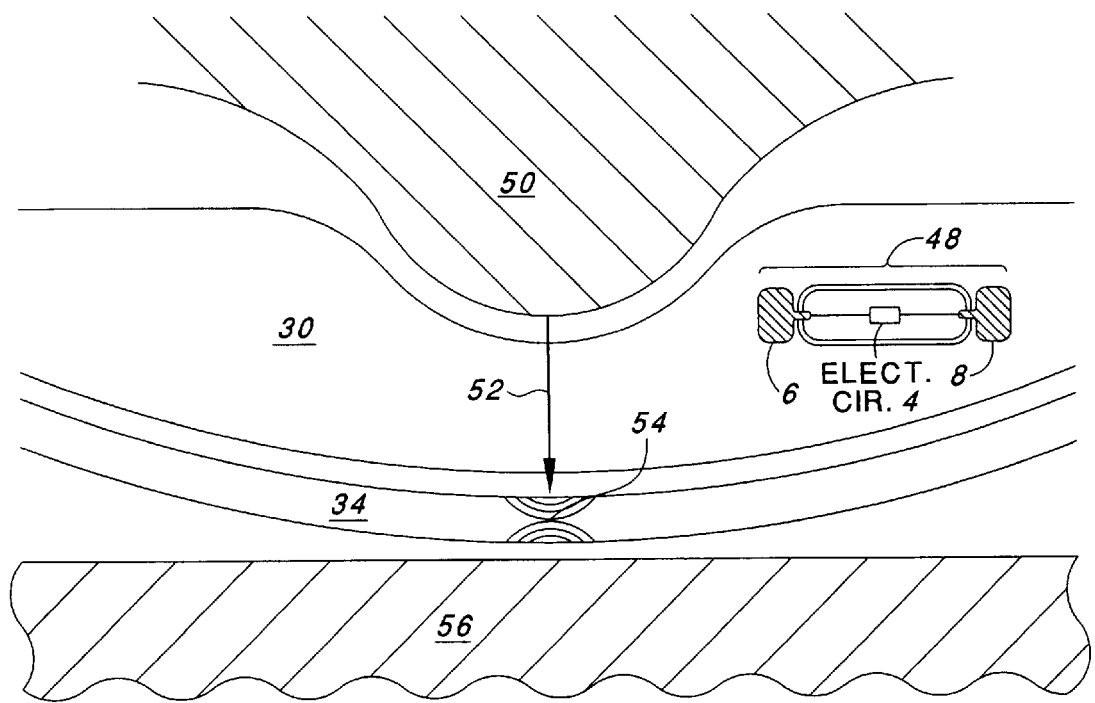
FIG. 8 illustrates the general circumstances that give rise to pressure ulcers, and illustrates one preferred manner in which an implanted microstimulator, in accordance with the present invention, may be used to reduce pressure ulcer formation.

As stated above, the microstimulators provided herein are particularly useful in the prevention and treatment of various disorders associated with prolonged immobilization or confinement; such as muscle atrophy, pressure ulcers and venous emboli. Referring to FIG. 8, there is illustrated, in diagrammatic form, the general circumstances that give rise to pressure ulcers and a preferred embodiment whereby one or more microstimulators may be employed to reduce the incidence of and/or contribute to the healing of such pressure ulcers. As depicted in FIG. 8, force 52 applied between bone 50 and firm support surface 56 is transmitted through intervening soft tissues of the skin 34 and muscle 30, resulting in compression of skin region 54. Skin region 54 is thus in danger of developing a pressure ulcer. Active contraction of muscle 30 is induced by electrical stimulation applied by microstimulator 48 and its associated electrodes 6 and 8. Such active contraction makes muscle 30 stiffer, causing force 52 to be dissipated over a larger region of the skin 34. Further, active contraction of muscle 30 tends to shift the position of the body with respect to surface 56, causing force 52 to be directed to a fresh region of skin 34. Regular active contraction of muscle 30 induces various trophic mechanisms in the muscle that maintain or even enhance the bulk and tone of muscle 30 in its passive state, thereby reducing the concentration of force 52 on skin region 54.

To further aid in the prevention and/or treatment of the pressure ulcer, the microstimulator as described above and illustrated in FIGS. 3–6 employing a coating 10 having a chemical agent 20 associated therewith, may be used. In this alternative, the chemical agent 20 may be a trophic factor employed to improve the bulk and tone of the muscle 30 or may be an antibiotic or similar therapeutic drug useful for preventing infection of the pressure ulcer, or the chemical agent may be a combination of the two different agents. Increasing the bulk and tone of the muscle 30, can provide additional padding between the bone 50 and support surface 56, thereby lessening the force 52 against the skin region 54.

In the embodiment illustrated in FIG. 8, a microstimulator 48 has been injected into muscle 30 at (or very near) the skin region site 54 where a potential pressure ulcer may develop. However, it may be satisfactory (or even preferred in some instances) to inject one or more microstimulators into adjacent muscles or near various nerves that control muscle 30 and/or other muscles that can affect the magnitude and direction of force 52 upon various regions of skin 34.

It should be appreciated that contraction of many different muscles and groups of muscles tends to lift the prominence of bone 50 so as to distribute the load of the body more evenly across the skin 34, thereby reducing the amount of force 52 applied at a particular skin region 54. Optimally, a particular temporal pattern of stimulation applied by one or more microstimulators generates a sustained contraction of the respective muscles that is maintained for several seconds to permit blood flow into vulnerable tissues. Such is accomplished by the extracorporeal components illustrated in FIG. 5 and described above. Thus, upon an external command, or at predetermined intervals, power and command signals sent from controller 40 cause the various microstimulators to emit a series of electrical current pulses (i.e., a pulse train) at the desired frequency and amplitude sufficient to cause the muscles to lift the body for the duration of the pulse train.

Further movement of the body part typically occurs after cessation of such pulse-train stimulation because of various nervous reflexes or voluntary movements that are triggered by the concomitant activation of various sensory nerve fibers resulting either from direct electrical stimulation of the sensory fibers or the mechanical consequences of the directly stimulated muscle activity. Such triggered movements are generally just as important, and may even be more important, than the directly stimulated muscle activity caused by the microstimulator-generated pulse train for shifting body posture.

Figure 9:
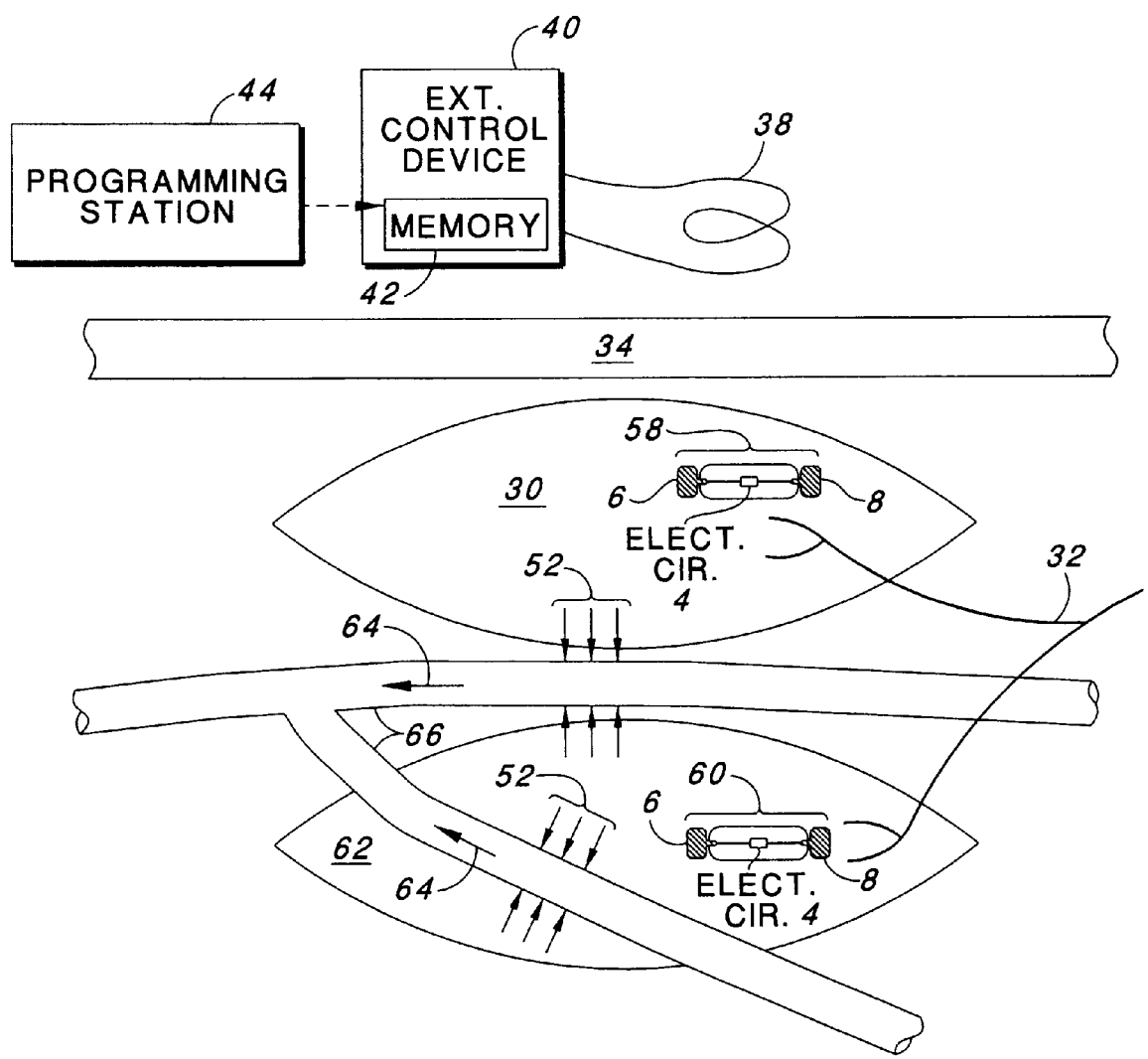
FIG. 9 illustrates the general circumstances that give rise to venous stasis, and further shows a preferred manner in which an implanted microstimulator may be used and controlled, in accordance with the present invention, to prevent and treat such a condition.

FIG. 9 illustrates the general circumstances that give rise to venous stasis and a particular embodiment for the use of microstimulators to reduce such stasis. Blood flow 64 in veins 66 running through and between muscles 30, 62 depends in part on compressive forces 52 and general metabolic stimulation resulting from the occasional active contraction of muscles 30 and 64. In the absence of such contractions, flow is reduced, resulting in stasis and an increased likelihood of the formation of clots or thrombi in the veins. One common site for this problem is in the calf muscles of the lower leg, which extend the ankle. In accordance with one aspect of the present invention, therefore, one or more microstimulators are injected into the extensor muscles of the ankle, and one or more microstimulators are injected into the flexor muscles of the ankle. The programmed sequence of stimulation stored in memory bank 42 is used by controller 40 to create the necessary transmission of power and command signals from coil 38 to cause the microstimulators injected into the ankle muscles to generate a prescribed stimulation sequence. Ideally~this prescribed sequence elicits muscle contractions sufficient to shift the position of the foot alternately into extension and flexion for several seconds. The interval between the various muscle contractions and the strength and duration of the contraction in each muscle is set by an attending physician or physiotherapist using a programming station 44 that downloads the desired program into memory bank 42. The rhythmic intermittent muscle contractions produced each time the program is activated causes compressive forces to act on deep veins 66, augmenting venous flow 64 out of the muscle by a pumping action that reduces venous stasis.

It should also be noted that a particular pattern of stimulation applied through a particular microstimulator, or combination of microstimulators, may also be effective at reducing the incidence of both pressure sores and venous stasis simultaneously, as well as generating other useful trophic effects on the muscles themselves, metabolic stimulation of the cardiorespiratory system, and improvements in the functioning of nervous pathways responsible for various reflexive and autonomic functions commonly affected adversely by prolonged immobilization. Other specific dysfunctions that have been reported to be reduced by regular electrical stimulation of nerves and muscles include autonomic dysreflexia and sensorimotor spasticity, particularly in patients suffering from spinal cord injury.

It should also be noted that the particular complications of pressure sores and venous stasis illustrated respectively in FIGS. 8 and 9 are intended only to provide specific examples of the beneficial effects of regular, active muscle exercise that can be induced by microstimulators, and are not intended to limit the scope of the invention set forth in the claims regarding the utility of stimulation applied in this manner. The present invention pertains generally to all beneficial effects that a caregiver might achieve by the appropriate implantation and programming of one or more microstimulators in any patient immobilized for a period of more than a few days.

While the invention herein disclosed has been described by means of specific embodiments and applications thereof, numerous modifications and variations could be made thereto by those skilled in the art without departing from the scope of the invention as set forth in the claims.

What is claimed is:

1. A system for the prevention or reversal of one or more disorders associated with inactivity, immobilization or confinement of one or more muscles, the system comprising:

(a) at least one implantable microstimulator comprising a hermetically-sealed housing, at least two exposed electrodes for providing electrical current, and electronic means within said hermetically-sealed housing for generating electrical current applied to said exposed electrodes, wherein each at least one implantable microstimulator is of a size and shape capable of implantation by expulsion through a narrow cannula, and wherein said at least one implantable microstimulator is coated with a polymeric coating over a substantial portion of the surface area of the hermetically-sealed housing, and wherein the polymeric coating includes a chemical agent therein that diffuses from the surface of the coating into the surrounding tissue;

(b) implantation means useful for implanting said at least one implantable microstimulator into muscle tissue so as to be proximate to a motor nerve fiber;

(c) external control means for commanding the at least one implanted microstimulator to produce various stimulation pulses until a desired stimulation sequence and pattern are identified, said external control means having a memory element;

(d) storage means for storing the desired stimulation sequence and pattern in the memory element of the external controller; and (e) trigger means for triggering the desired stimulation sequence and pattern from the external controller to provide regular electrically-induced contraction of the muscle each time such is desired.

2. A system for reducing the incidence of disorders and medical complications resulting from physical confinement or immobilization of the whole body or parts thereof, comprising:

at least one implantable microstimulator comprising a hermetically-sealed housing, at least two exposed electrodes, electronic means within said hermetically-sealed housing for generating an electrical current and applying said electrical current to said at least two exposed electrodes, and a battery for providing operating power to the at least one implantable microstimulator means for implanting the at least one implantable microstimulator in muscle associated with an affected site; and means for administering prescribed sequences of electrical stimulation through the at least two exposed electrodes of the at least one implantable microstimulator to nerves or muscle in the vicinity of the at least one implantable microstimulator comprising:

means for preprogramming said at least one implantable microstimulator with a desired sequence and pattern of electrical simulation; and means for activating said desired sequence and pattern of electrical stimulation at prescribed intervals.

\* \* \* \* \*